United States Patent

Kee et al.

Patent Number: 5,357,946
Date of Patent: Oct. 25, 1994

[54] VENTILATOR MANIFOLD WITH ACCESSORY ACCESS PORT AND ADAPTORS THEREFORE

[75] Inventors: Kok-Hiong Kee; James G. Schneider, both of St. Louis, Mo.

[73] Assignee: Sherwood Medical Company, St. Louis, Mo.

[21] Appl. No.: 80,276

[22] Filed: Jun. 21, 1993

Related U.S. Application Data

[63] Continuation-in-part of Ser. No. 962,755, Oct. 19, 1992, Pat. No. 5,333,607.

[51] Int. Cl.$^5$ ............................................. A61M 16/00
[52] U.S. Cl. ........................... 128/200.24; 128/204.18; 128/200.23; 128/203.12; 128/205.13; 128/912
[58] Field of Search .................. 128/204.18, 911, 912, 128/200.23, 202.27, 203.12, 200.22, 205.13, 207.14, 207.16, DIG. 26, 200.24; 604/171, 172, 247, 167, 169; 285/331, 332, 330, 332.1

[56] References Cited

U.S. PATENT DOCUMENTS

| | | | |
|---|---|---|---|
| 954,519 | 4/1910 | Kelly | 128/207.15 |
| 1,588,336 | 6/1926 | Richmond | 285/331 X |
| 3,416,567 | 12/1968 | Von Dardel et al. | 137/604 |
| 4,240,417 | 12/1980 | Holever | 128/203.12 |
| 4,346,702 | 8/1982 | Kubota | 128/207.14 |
| 4,351,328 | 9/1982 | Bodai | 128/202.16 |
| 4,426,062 | 1/1984 | Bowron | 251/7 |
| 4,475,548 | 10/1984 | Muto | 128/207.14 |
| 4,484,577 | 11/1984 | Sackner et al. | 128/203.28 |
| 4,510,933 | 4/1985 | Wendt et al. | 128/207.14 |
| 4,569,344 | 2/1986 | Palmer | 128/207.16 |
| 4,580,556 | 4/1986 | Konour | 128/206.28 |
| 4,781,702 | 11/1988 | Herrli | 604/244 |
| 4,805,611 | 2/1989 | Hodgkins | 128/207.14 |
| 4,836,199 | 6/1989 | Palmer | 128/207.16 |
| 4,850,350 | 7/1989 | Jackson | 128/207.16 |
| 4,857,062 | 8/1989 | Russell | 604/256 |
| 4,938,210 | 7/1990 | Shene | 128/203.12 |
| 4,951,661 | 8/1990 | Sladek | 128/202.27 |
| 5,009,391 | 4/1991 | Steigenwald | 251/149.1 |
| 5,025,806 | 6/1991 | Palmer et al. | 128/203.12 |
| 5,083,561 | 1/1992 | Russo | 128/207.16 |
| 5,158,569 | 10/1992 | Strickland | 604/283 |
| 5,178,138 | 1/1993 | Walstrom et al. | 128/200.23 |
| 5,215,522 | 6/1993 | Page et al. | 604/33 |
| 5,269,756 | 12/1993 | Dryden | 604/54 |

FOREIGN PATENT DOCUMENTS

0414997  3/1991  European Pat. Off.

Primary Examiner—Edgar S. Burr
Assistant Examiner—Eric P. Raciti
Attorney, Agent, or Firm—Andrew J. Beck; Montgomery W. Smith; Gene B. Kartchner

[57] ABSTRACT

A ventilator manifold and adaptors therefore are disclosed which allow attachment of respiratory system accessory devices to the ventilator manifold without loss of PEEP. The manifold includes an accessory access port which has a normally closed valve therein which remains closed regardless of the pressure changes within the manifold. The normally closed valve is positioned in the accessory access port such that placement of an adaptor therein forces the normally closed valve to an open position, and removal of the adaptor allows the normally closed valve to return to its closed position. The adaptors are formed to allow attachment of accessory devices such as an ambulatory resuscitation bag, a metered dose inhaler, and a bronchial scope. The adaptors may also include a locking ring thereon for locking the adaptor in position in the accessory access port. Further, the manifold and adaptors may also be designed to allow the injection of fluid through the accessory access port into the manifold for cleaning or lavage.

12 Claims, 6 Drawing Sheets

VENTILATOR MANIFOLD WITH ACCESSORY ACCESS PORT AND ADAPTORS THEREFORE

This application is a Continuation-in-Part of co-pending U.S. Pat. application Ser. No. 07/962,755 filed Oct. 19, 1992, titled "Ventilator Manifold with Accessory Access Port", now U.S. Pat. No. 5,333,607.

BACKGROUND OF THE INVENTION

1. Field of the Invention

This invention relates generally to apparatus used in conjunction with respiratory support systems. More specifically, the present invention relates to a method and apparatus for the attachment of accessory devices to a respiratory support system. Even more specifically, the present invention relates to a ventilator manifold and adaptors therefore which accommodate the attachment and detachment of accessory devices to the system.

2. Prior Art

Respiratory systems used for the ventilation of critically ill patients are now commonly used in medical facilities. Typically, a prior art respiratory system includes a tracheal tube, positioned either directly or through the nose or mouth into the trachea of a patient, a manifold connected to the tracheal tube at one port position thereof, and a source of breathable gas connected at a second port thereof. The purpose of the respiratory system is to assist the patient in maintaining adequate blood oxygenation levels without over taxation of the patient's heart or lungs.

While a patient is attached to a respiratory system, it is periodically necessary to enter the manifold with various accessory devices such as a suction catheter, metered dose inhaler, manual resuscitation bag, bronchoscope, or the like. In the past, it has been necessary to disassemble part of the respiratory system, either by removing the manifold, or by opening a port thereof, to insert an accessory device through the tracheal tube and into the patient's trachea and lungs. Due to the interruption in respiratory support resulting from this procedure, a patient's blood oxygen can drop to an unacceptably low level, even if other previously known breathing assisting efforts are simultaneously provided.

One solution to the above problem, which is generally exemplary of the prior art, is shown in U.S. Pat. No. 5,073,164 by Hollister et al. in which the ventilator manifold includes a port thereon which is adapted to receive a connector of a suctioning device. The suctioning device positions a suction catheter within the manifold without substantial manifold pressure loss. Although this type of ventilator manifold and suctioning device connection allows continuous respiratory support of the patient during suctioning of fluid from the patient's trachea and lungs, there nevertheless remain several drawbacks associated with its use. For example, removal of the suctioning device from the manifold, such as for the purpose of replacing the suctioning device or attaching another accessory to the manifold, e.g. a manual resuscitation bag or a metered dose inhaler, etc., cannot be accomplished without loosing manifold pressure and compromising the integrity of the respiratory system. Thus, respiratory support of the patient must be stopped whenever the suctioning device is removed from the manifold.

U.S. Pat. No. 4,351,328 to Bodai attempts to solve this problem by forming an opening in the ventilator manifold which is blocked by a pre-punctured resilient seal through which a suction catheter can be passed without substantially affecting the integrity of the system, i.e., without substantial gas exchange or pressure loss between the interior of the manifold and the atmosphere. The Bodai device, although allowing entry and removal of a suction catheter through a ventilator manifold during continuous respirator support of a patient, nevertheless fails to completely resolve the existing problem in the prior art. Specifically, there is no design consideration for the attachment of other accessory devices, such as a manual resuscitation bag or a metered dose inhaler, which are often necessary for use in the care of a patient.

There therefore exists a need in the art for a respiratory system which includes a ventilator manifold and adaptors which allow simple attachment and detachment of accessory devices with the manifold without substantial pressure loss from the system.

OBJECTS AND SUMMARY OF THE INVENTION

A principle object of the present invention is to provide a patient respiratory system which allows access thereto of accessory devices.

Another object of the present invention is to provide a respiratory system which allows access of accessory devices thereto through an accessory access port within the manifold which is normally closed against the atmosphere and which will open upon attachment of the accessory device and automatically reclose upon detachment thereof.

A further object of the present invention is to provide a respiratory system having a manifold which includes an accessory device access port with a normally closed valve therein, which can accommodate an adaptor formed to be usable with an accessory device and designed to open the normally closed valve and seal against the port, the normally closed valve allowing interchangeable use of accessory devices within the manifold while maintaining manifold pressure integrity.

Another object of the present invention is to provide a manifold for a respiratory system which includes an accessory device access port which is adapted to allow cleaning fluid to be injected therein in order to clean the adaptor and accessory device while positioned within the access port.

These and other objects of the present invention are realized in a presently preferred embodiment thereof, described by way of example and not necessarily by way of limitation, which provides for interchangeable use of accessory devices with a manifold of a respiratory system during respiratory support of a patient, without comprising the integrity of the system by causing significant pressure loss through the manifold. The invention includes a ventilator manifold formed with an accessory device access port which includes a normally closed valve therein. The valve maintains the pressure differential between the atmosphere and the interior of the manifold regardless of manifold pressure fluctuations. The accessory device access port also includes a sleeve member positioned within the port, so as to line the port interior surface, which assists in sealing against an adaptor inserted into the port. The sleeve member also passes through a side opening in the port and attaches to a pigtail type fluid injection tube which is adapted for allowing injection of fluid therethrough into the access port and through the sleeve member into the adaptor. The pigtail may also include a one-way valve therein for preventing retrograde movement of fluid therethrough.

The invention also includes an adaptor which is formed to fit within the accessory device access port and sealingly engage with the sleeve member and the normally closed valve. Positioning the adaptor into the access port forces the normally closed valve to an open position. The adaptor may include a detent and stop-type locking arrangement for locking the adaptor within the port against inadvertent withdraw thereof during use, and for properly orienting the adaptor within the port to form a clear passage through the port and adaptor for the insertion and removal of a medical instrument. The adaptor may also include a side opening therein which is orientable relative to the stop-type locking mechanism on the adaptor to cause it to align with the side opening of the sleeve member and the access port when the adaptor is properly position within the access port and locked in place for use.

The adaptor locking mechanism and the access port are designed to ensure that the adaptor can be inserted and locked into the access port in only one unique orientation therewith so as to ensure that the side opening of the adaptor is in alignment with the side opening of the sleeve member and the access port. In this manner, cleaning fluid may be injected through the fluid injection tube directly to the interior of the adaptor whenever the adaptor is properly locked in position within the access port. Any medical instrument or portion thereof located within the adaptor therefore can easily be cleaned without the necessity of removing the adaptor from the access port.

The adaptor may be modified to allow its use with, any one of a number of common respiratory system accessories, such as a metered dose inhaler, a manual resuscitation bag, a bronchoscope, or the like.

If desired, the manifold of the present invention may also include swivel connectors at the patient attachment port and the ventilator circuit connection port thereof to allow rotation of the manifold relative to the trachea tube and/or the flexible breathing hoses from the respiratory system in order to increase the patient's comfort during use.

These and other objects and advantages of the present invention will become apparent from the following more detailed description, when taken in conjunction with the accompany drawings, in which like elements are identified with like numerals throughout.

DETAILED DESCRIPTION OF THE PREFERRED EMBODIMENTS

As shown in the exemplary drawings for the purposes of illustration, an embodiment of a ventilator manifold made in accordance with the principles of the present invention, referred to generally by the reference numeral 10, is provided for interchangeable access of respiratory system accessory devices.

Figure 1:
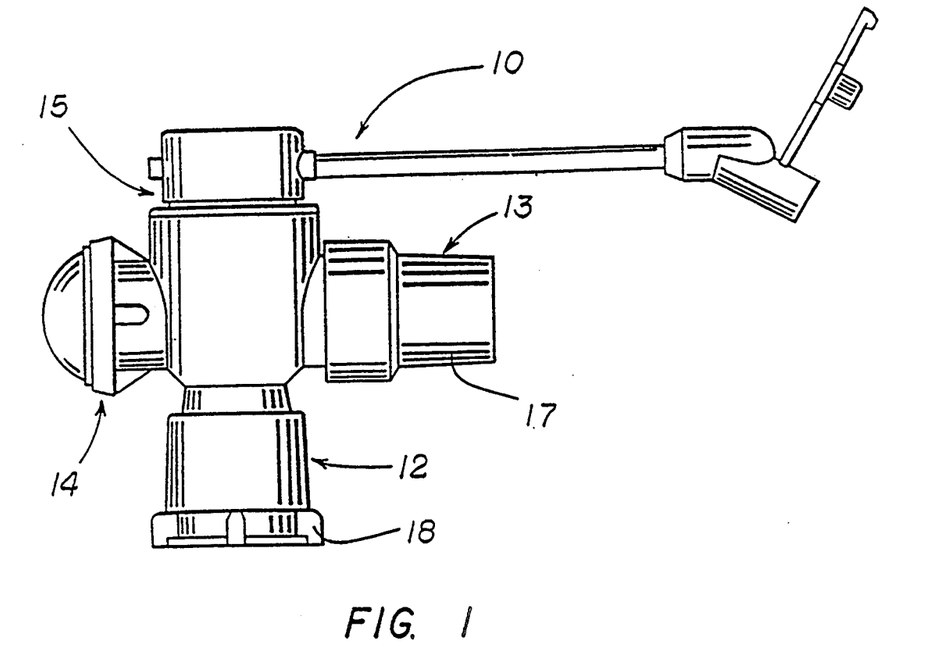
FIG. 1 shows a ventilator manifold of a respiratory support system which has been modified to include an accessory device access port formed in accordance with the principles of the present invention.

More specifically, as shown in FIG. 1, the ventilator manifold 10 of the present invention includes a plurality of access ports which facilitate its connection to a patient and to a ventilator circuit of the respiratory system. The manifold 10 is attached to a patient for fluid flow communication with the patient's lungs by the connection of the patient attachment port 12 thereof to the connector of an endotracheal tube assembly (not shown) which has been previously positioned in the trachea of a patient by any one of several well known procedures.

The weaning port 14 is normally kept covered by a cap, and the ventilator circuit connection port 13 of the manifold 10 is connected to flexible breathing hoses from the respiratory system (not shown) in a well known manner, such as through a "Y" site connector.

The ventilator circuit connection port 13 and the patient attachment port 12 may, if desired, include swivel connectors 17 and 18 respectively thereon in order to allow relative rotation between the manifold 10 and the trachea tube breathing hoses (not shown). The swivels 17 and 18 operate to isolate the trachea tube from forces thereon caused by the manifold 10 or the breathing hoses. Isolation of the trachea tube in this manner increases the comfort of the patient when attached to the respiratory system.

The ventilator circuit attached to port 13 provides a high oxygen content gas mixture to the patient and receives the expelled air from the patient. The ventilator circuit commonly includes various valves, regulators and the like associated with the hoses attached to the port 13 which aid in effecting respiration of the patient. The manifold 10 and hoses attached thereto at the ventilator circuit connection port 13 are generally made of disposable plastic material and are intended to be used by only one patient and then discarded.

When attached to the patient, the entire respiratory system is designed to isolate the patient's lungs from the atmosphere and allow pressurized forced ventilation of a gas mixture of a high oxygen content from the ventilator into the patient's lungs. Commonly, respiratory systems of this type are used to maintain a positive end expiratory pressure (PEEP) within the ventilator manifold 10 and the patient's lungs at all times during exhalation. This technique is used because of its benefit of ensuring that a minimum concentration of oxygen is supplied to the patient to maintain proper blood oxygenation levels. The PEEP procedure keeps a large number of lung alveoli of the patient open at all times during respiratory support, thus increasing the effective lung area subject to ventilation.

Prevailing respiratory support techniques, including PEEP, have made it very disadvantageous to interrupt respiratory support of the patient by removing the manifold 10 from the patient or opening it to the atmosphere. Therefore, the repeated attachment and detachment of accessory devices for necessary medical procedures has had to be avoided because of the loss of isolation of the respiratory system from the atmosphere during these procedures, and the immediate loss of effective lung surface area due to alveoli collapse. Further, when such procedures take an extended period of time to perform, blood oxygen can drop to inadequate levels, and cause the patient to over exert his or her lungs and heart when trying to return blood oxygenation levels to normal. Also, disassembly and reassembly of the respiratory system for procedures with prior art accessory devices has in the past been very time consuming for the medical worker.

The present invention resolves the problems associated with loss of isolation of the respiratory system from the atmosphere (i.e. loss of PEEP) when these various accessory devices must be attached or detached from the manifold 10 for use in performing necessary medical procedures during respiratory support. Specifically, the manifold 10 of the present invention has been formed to include an accessory device access port 15 which is in fluid flow communication with the interior of the manifold 10 and the atmosphere and which can be accessed without loss of PEEP.

Figure 2:
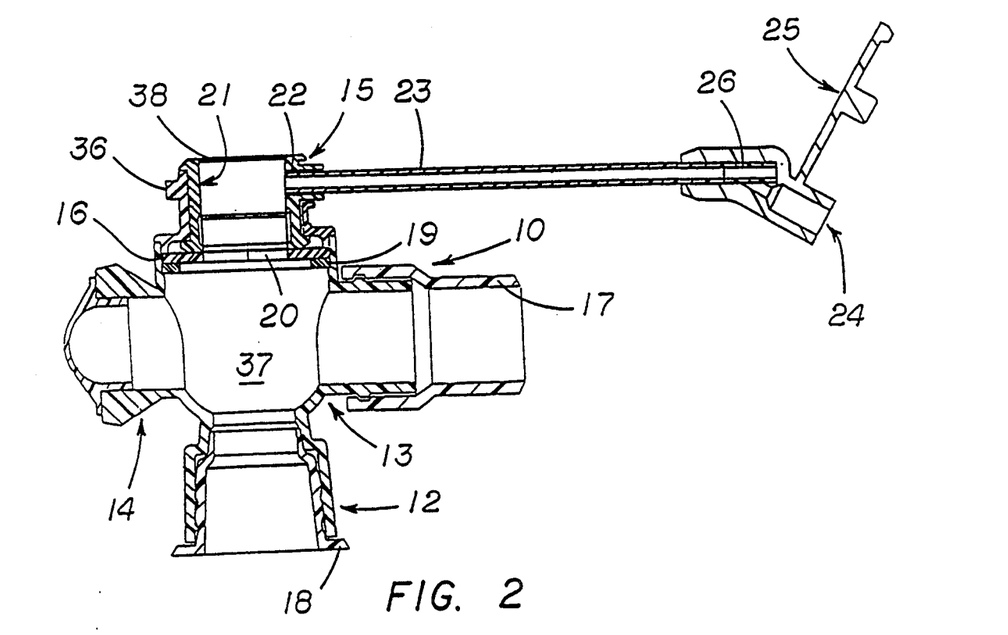
FIG. 2 shows a cross-sectional view of the ventilator manifold of FIG. 1.

As best shown in FIG. 2, the access port 15 includes a normally closed valve 16 formed therein which maintains the interior of the manifold 10 isolated from the atmosphere at all times. As explained above, the interior of the manifold 10, although experiencing constant pressure fluctuations, is generally kept at a pressure which is slightly above atmospheric pressure in order to properly administer oxygen according to the PEEP procedure. The valve 16 is preferably made of a resilient material to ensure that pressure isolation of the manifold 10 is maintained.

The valve 16 is preferably formed into a circular disk shape and inserted into the manifold 10 between the access port 15 and a support ring 19. The valve 16 is formed with one or more slits 20, which are normally closed against fluid flow therethrough, but may be forced opened by the insertion of an adaptor therein as will be explained below.

The interior of the access port 15 is lined with a sleeve member 21 which covers the entire interior surface of the access port 15 and abuts in sealing relationship against the normally closed valve 16. The interior diameter of the sleeve member 21 is predetermined to cause a snug fit with an adaptor to assist in the prevention of leakage from the manifold 10 when the normally closed valve 16 is forced opened thereby.

The access port 15 forms a side opening 22 through which a portion of the sleeve 21 extends to be attached, such as by solvent bonding, to a pigtail fluid injection tube 23. The injection tube 23 is intended for use in transporting fluid through the access port side opening 22 into the interior of the access port 15. The opposite end of the pigtail tube 23 includes a luer connector 24 with an integrally formed luer connector plug 25. If desired, a check valve 26, taking the form of a collapsible sleeve, may be positioned between the luer connector 24 and the pigtail tube 23 which collapses upon injection of fluid through the luer connector 24 in the direction of the pigtail tube 23, but expands to block fluid flow in the opposite direction.

It is preferred that the sleeve member 21 be formed of a relatively flexible material such as plasticized PVC having good solvent bonding characteristics, with the material forming the pigtail tube 23 preferably being formed of the same material as the sleeve member 21. The access port 15 according to the preferred embodiment of the present invention is formed of clear ABS, which is preferably the same material forming the main body of the manifold 10 in order to ensure good ultrasonic or solvent bonding therebetween.

Figure 3:
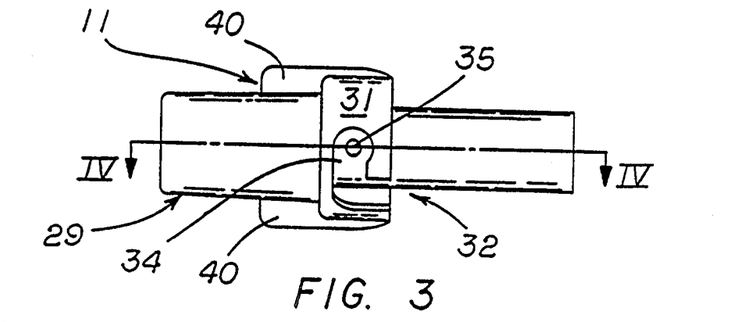
FIG. 3 is a first embodiment of an adaptor formed in accordance with the principles of the present invention which is useful in conjunction with an ambulatory resuscitation bag.
Figures 4, 6, 7:
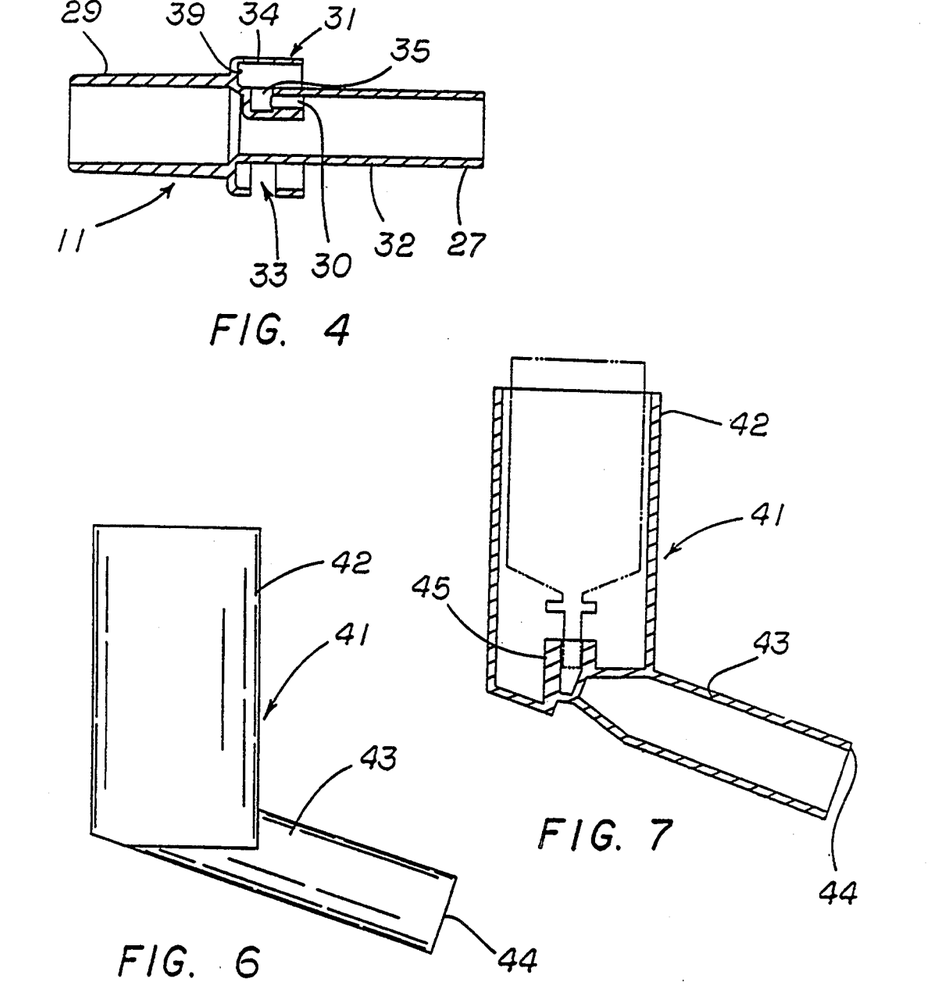
FIG. 4 is a cross-sectional view of the adaptor taken along line IV—IV of FIG. 3.
FIG. 6 is a second embodiment of an adaptor formed in accordance with the principles of the preset invention which is useful in conjunction with a metered dose inhaler.
FIG. 7 is a cross-sectional view of the adaptor of FIG. 6.

FIGS. 3 and 4 show a first embodiment of the adaptor of the present invention adapted for use with an ambulatory resuscitation bag, and identified generally by the reference numeral 11. The adaptor 11 is formed in a generally tubular shape, with one end forming an ambulatory resuscitation bag attachment extension 29 and the other end forming an insertion member 32. The attachment extension 29 is sized to allow air tight attachment thereof with a standard ambulatory resuscitation bag (not shown) in a well-known manner. The ambulatory resuscitation bag used with the adaptor 11 of the present invention preferably includes its own internal valving system to allow it to inject air through the adaptor 11 and subsequently received expelled air from the adaptor 11 and vent the expelled air to the atmosphere. A pair of wings 40 may be formed to extend from the attachment extension 29 to facilitate gripping of the adaptor 11 for attachment thereof to the ambulatory bag and the manifold 10.

Figure 5:
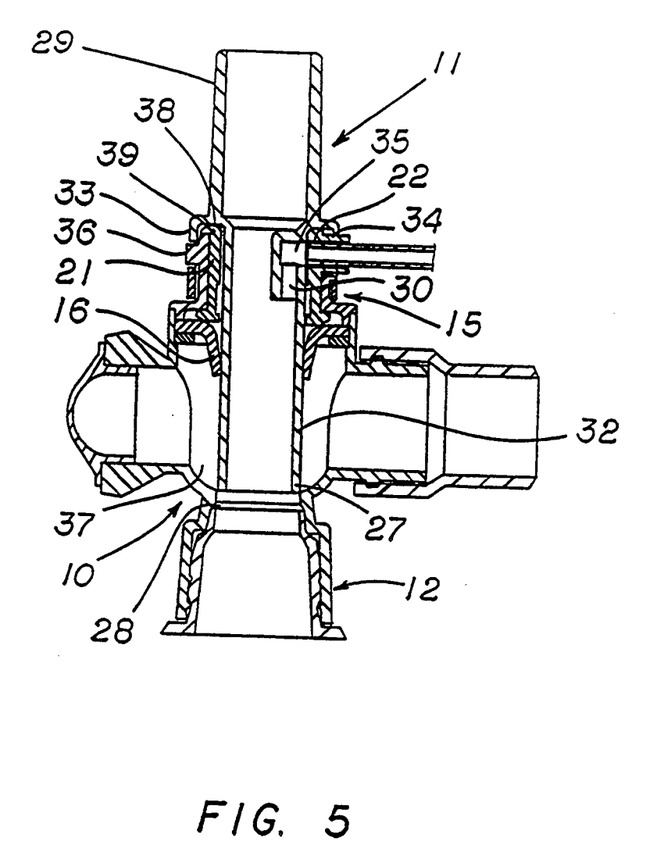
FIG. 5 is a cross-sectional view of the first embodiment of the adaptor positioned within the manifold of the present invention.

A locking cylinder 31 may be formed to encircle a portion of the adaptor insertion member 32 and include a pair of arcuate slots 33 and 34 which operate together as a locking mechanism to ensure secure attachment of the adaptor 11 to the access port 15 of the manifold 10, and also ensures proper relative orientation therebetween to cause an opening 35 in the insertion member 32 to be positioned in alignment with the side opening 22 of the access port 15 when the adaptor 11 is properly locked in position therein for use as best shown in FIG. 5.

As can be seen in FIG. 5, the arcuate slot 33 is sized to be engageable with the nub 36 which is located directly opposite the side opening 22 on the access port 15. The arcuate slot 34 is larger in width than the arcuate slot 33 and therefore can accommodate the side opening 22 of the access port 15. As is readily evident, since the arcuate slots 33 and 34 are sized differently to accommodate the nub 36 and the side opening 22 respectively of the access port 15, the adaptor 11 can only lock in position within the access port 15 in one unique relative orientation therewith in which the insertion member opening 35 and the side opening 22 are in alignment.

Attachment of the adaptor 11 to the respiratory manifold 10 is effected by insertion of the adaptor 11 into the access port 15 until the insertion member 32 engages the valve 16 and forces it toward the interior of the manifold 10. Upon complete insertion of the adaptor 11 into the port 15, the valve 16 is completely open and the sleeve member 21 is sealingly engaged with the insertion member 32. Also, the sleeve shoulder 38 of the sleeve member 21 is forced to resiliently deform within the base 39 of the locking cylinder 31. This increases the air tight seal and assists in positively locking the adaptor 11 to the access port 15 by forcing the arcuate slots 33 and 34 against the nub 36 and side opening 22 respectively.

It is intended that during insertion of the adaptor 11 into the access port 15, the sealing relationship formed between the sleeve member 21 and the insertion member 32 commence prior to opening of the valve 16 in order to ensure isolation of the interior of the manifold 10 from the atmosphere during attachment of the accessory device. Once completely inserted within the port 15, the distal end 27 of the insertion member 32 extends completely through the access port 15 and the manifold central chamber 37 to contact the port seat 28 of the patient attachment port 12.

Operation of the adaptor 11 of the present invention is straightforward. First, an ambulatory resuscitation bag is attached to the extension 29 and then the adaptor insertion member 32 is inserted into the accessory access port 15 of the manifold 10 until the distal end 27 thereof contacts the port seat 28 in the manifold central chamber 37 to effectively form an air-tight passage between the ambulatory bag and the patient's trachea and lungs, preventing any air flow to the patient from the atmosphere or from the respiratory system. The adaptor 11 is then rotated so that the locking ring 31 thereof locks against the nub 36 and the side opening 22 of the manifold 10. Air is then forced from the ambulatory resuscitation bag through the adaptor 11 and through the patient connection port 12 of the manifold 10 into the patient's trachea and lungs. Exhaled air then passes out of the patient's trachea and lungs through the connection prot 12 and the adaptor 11 to be vented to atmosphere by the ambulatory resuscitation bag. This process is repeated as desired.

If desired, fluid may be injected through the pigtail tube 23, and into the adaptor insertion member 32 through the opening 35 and injection fluid channel 30 thereof, and then through the patient connection port 12 into the trachea and lungs of the patient for purposes of medication or lavage.

When it is desired to remove the adaptor 11 from the manifold 10, it is only necessary to unlock the adaptor 11 from the access port 15, and withdraw the insertion member 32. Due to the resilient nature of the valve 16, upon withdrawal of the adaptor 11, it will return to its normally closed position without exposure of the interior of the manifold 10 to the atmosphere.

FIGS. 6 and 7 show a second embodiment of the adaptor of the present invention, referred to by numeral 41, which is adapted for use with a metered dose inhaler. The adaptor 41 is a generally tubular member having a proximal end which forms a receiving chamber 42 which is sized to loosely receive a standard sized metered dose injection canister (shown in dashed lines in FIG. 7). The distal portion is formed into an insertion member 43 having a distal end opening 44.

As best shown in FIG. 7, the receiving chamber 42 includes a canister nozzle retaining tube 45 which is adapted to receive the nozzle of the metered dose injection canister in a snug fit. The retaining tube 45 is in fluid flow connection with the insertion member 43 such that actuation of the metered dose injection canister in the well-known manner, with the canister nozzle positioned within the retaining tube 45, causes a metered dose of fluid to be ejected from the canister and forced through the insertion member 43 and out the distal end 44 thereof.

Although not shown on the adaptor 41, a locking ring such as described above in conjunction with the ambulatory resuscitation bag adaptor 11 (see element 31 in FIGS. 3 and 4), can be formed as part of the insertion member 43 of the adaptor 41 if desired.

Figure 8:
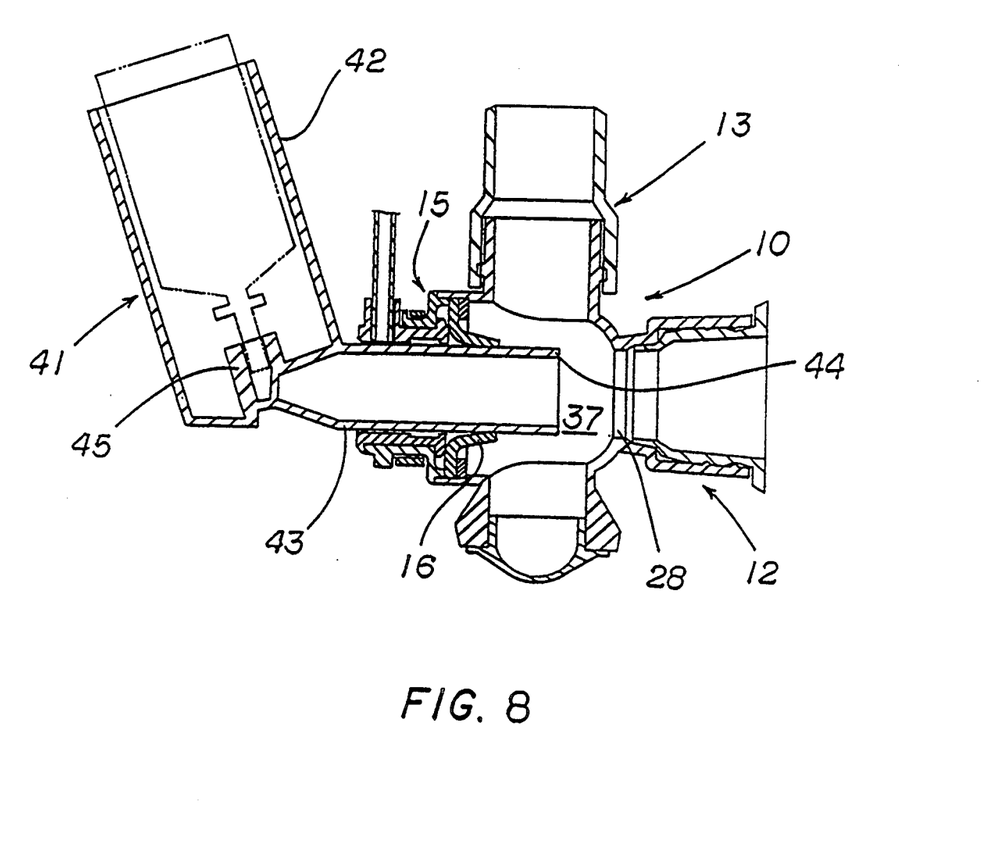
FIG. 8 is a cross-sectional view of the second embodiment of the adaptor positioned within the manifold of the present invention.

As shown in FIG. 8, the adaptor 41 is attached to the manifold 10 by forcing the insertion member 43 through the access port 15 and past the normally closed valve 16 to position the distal end 44 thereof within the central chamber 37. As opposed to the adaptor 11 described above in conjunction with the use of an ambulatory resuscitation bag, the insertion member 43 of the adaptor 41 does not pass completely through the central chamber 37 to seal against the port seat 28. Therefore, continued ventilation of the patient by the respiratory system through the ventilator circuit connection port 13 is allowed during use of the adaptor 41.

Once the adaptor 41 is positioned in the manifold 10 as shown in FIG. 8, the metered dose injection canister can be actuated to cause a metered dose of fluid, such as a medicament, to be injected into the manifold central chamber 37 where it is mixed with air from the ventilator circuit as it passes into the patient's lungs through the patient connection port 12.

When it is desired to remove the adaptor 41 from the manifold 10, it is only necessary to withdraw the insertion member 43 thereof from the access port 15 and allow the normally closed valve 16 to return to its normally closed position.

Figure 9:
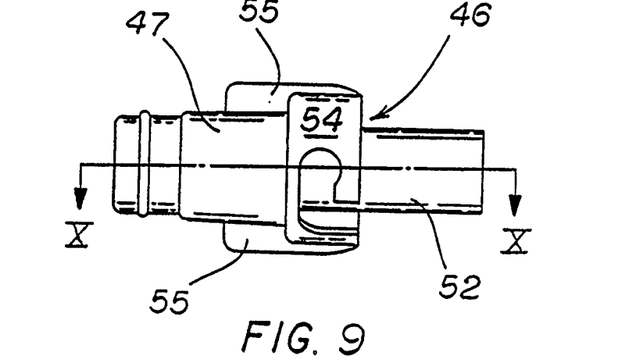
FIG. 9 is a third embodiment of an adaptor formed in accordance with the principles of the present invention which is useful with a bronchoscope.
Figure 10:
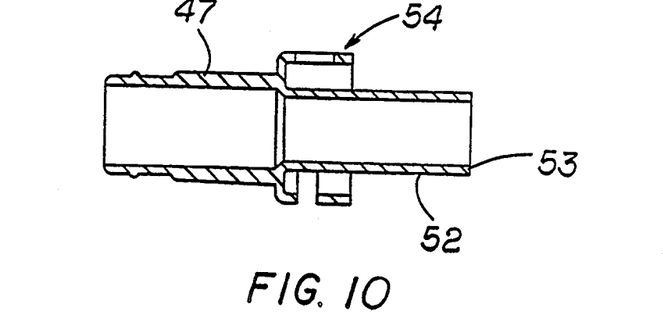
FIG. 10 is a cross-sectional view of the adaptor taken along line X—X of FIG. 9.
Figure 11:
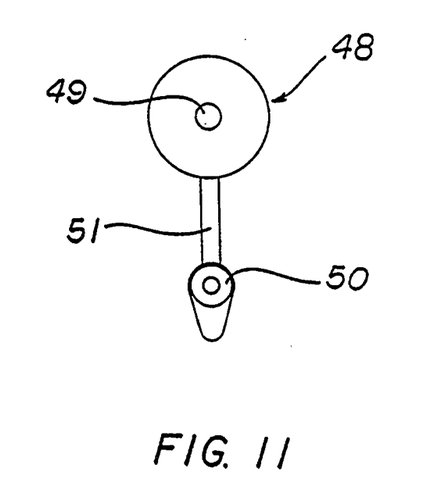
FIG. 11 is a top view of a cap member used in conjunction with the third embodiment of the adaptor of the present invention as shown in FIG. 9.

Referring now to FIGS. 9 through 11, a third embodiment of the adaptor of the present invention is shown which is modified for use with an endoscope. The endoscope adaptor 46 includes a proximal portion 47 which is adapted to receive a cap 48 in air-tight connection therewith. The cap 48 includes an opening 49 therethrough which is sized to a diameter slightly smaller than the diameter of the endoscope to be used therewith, to allow the endoscope to pass through the adaptor 46 and form an air-tight seal. The cap 48 can be formed with various sizes of openings 49 therethrough so that the adaptor 46 can be used with various sizes of endoscopes by attaching a cap 48 thereto having the proper sized opening 49 for the particular endoscope to be used.

Figure 12:
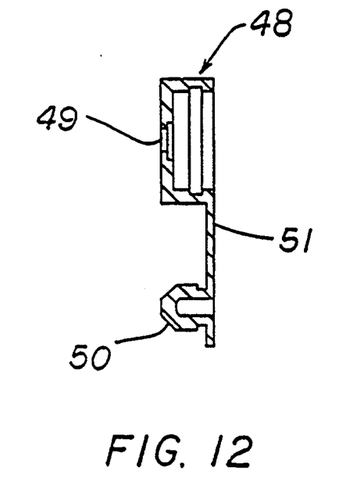
FIG. 12 is a cross-sectional view of the cap member of FIG. 11.

The cap 48 also includes a plug 50 which is preferably attached to the cap 48 by means of an elastomeric tether 51 and which is sized to plug the opening 49 when not in use.

As best shown in FIGS. 9 and 10, the distal portion of the adaptor 46 includes an insertion member 52 which forms an open distal end 53. The adaptor 46 also may include a locking ring 54 which operates in a manner identical to the locking ring 31 of the ambulatory resuscitation bag adaptor 11 described above. Similarly, the adaptor 46 may include wings 55 for assisting the user in attaching and detaching the adaptor 46 from the manifold 10.

Figure 13:
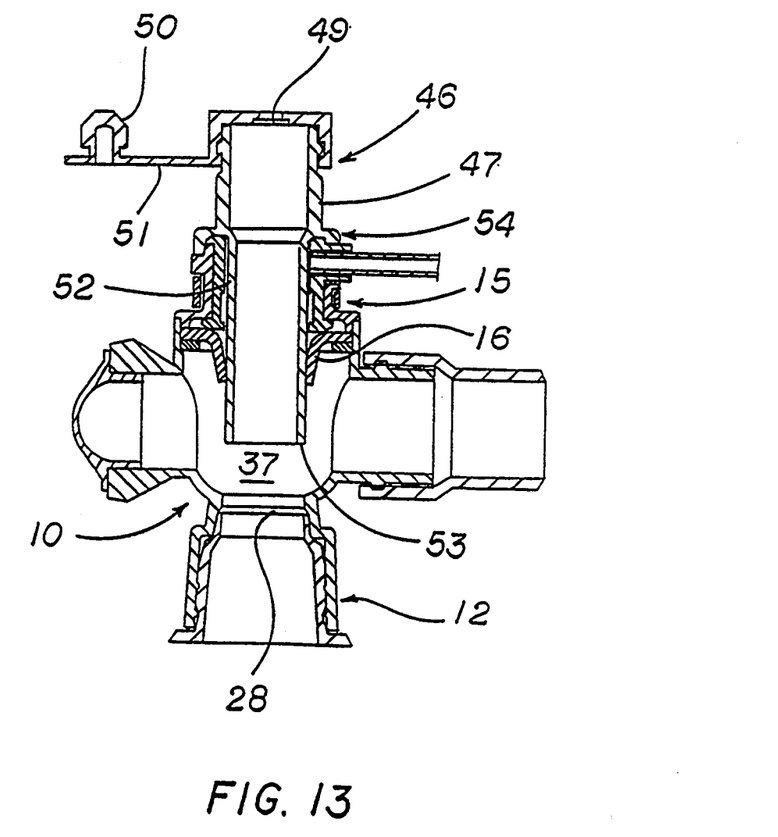
FIG. 13 is a cross-sectional view of the third embodiment of the adaptor positioned within the manifold of the present invention.

Referring now to FIG. 13, the endoscope adaptor 46 attaches to the access port 15 of the manifold 10 in a manner substantially identical to the manner of attachment of the ambulatory resuscitation bag adaptor 11 as described above, except that the distal end 53 of the insertion member 52 extends beyond the normally closed valve 16 and only partially into the manifold central chamber 37, and does not seal against the port seat 28. In this respect, the insertion member 52 is similar to the insertion member 43 of the metered dose inhaler adaptor 41 described above.

In use, the adaptor 46 is first fitted with a cap 48 having the desired size of opening 49 therethrough for the endoscope to be used. The plug 50 of the cap 48 is then inserted into the opening 49 and the adaptor 46 is attached to the manifold 10. When it is desired to insert the endoscope into the patient's trachea or lungs, the plug 50 is removed and the endoscope is immediately inserted into the opening 49 and through the adaptor and manifold into the patient.

When it is desired to remove the adaptor 46 from the manifold 10, the endoscope is removed from the opening 49 and the plug 50 is placed therein, the adaptor is then disconnected from the access port 15 and the valve 16 is allowed to return to its normally closed position.

It should be understood from the foregoing that, while particular embodiments of the invention have been illustrated and described, various modifications can be made thereto for adaption to various accessory devices which may be used in conjunction with a respiratory system which require access to a patient's lungs while maintaining isolation of the respiratory system from the atmosphere. It is to be understood that adaption of the present invention for use with any such accessory device is intended to be well within the spirit and scope of the present invention.

Also, although particular embodiments of the present invention have been shown, it is intended that the invention be limited only by the scope of the appended claims.

We claim:

1. The combination of a ventilator manifold for use with a respiratory support system, and an adaptor for a respiratory system accessory device, said manifold comprising:
    means for fluid flow connection between a patient and a ventilator circuit,
    means including an accessory access port for allowing attachment of said adaptor to said manifold, said accessory access port being normally closed against fluid flow therethrough into said manifold, said adaptor comprising a generally hollow tubular member having a proximal end and a distal end, said proximal end having means for releasably attaching to the respiratory system accessory device, and said distal end including opening means for opening said normally closed accessory access port.

2. The combination of claim 1 wherein said accessory access port includes a relatively flexible sleeve formed therein.

3. The combination of claim 1 wherein said accessory access port includes a normally closed valve therein, whereby, said normally closed valve is closed to fluid flow through said accessory access port and is forced to an open position by said opening means of said adaptor to allow fluid flow through said accessory access port when said adaptor is properly attached thereto.

4. The combination of claim 3 further including means for locking said adaptor to said accessory access port when said adaptor is properly attached thereto.

5. The combination of claim 1 wherein said opening means for opening said normally closed valve means further includes means for maintaining a seal between said adaptor and said accessory access port.

6. The combination of claim 5 wherein said proximal end of said adaptor includes means for receiving a metered dose injection canister.

7. The combination of claim 5 wherein said proximal end of said adaptor includes means for allowing insertion of an endoscope through said adaptor.

8. The combination of claim 7 wherein said means for allowing insertion of an endoscope forms an opening through which an endoscope may pass into said adaptor, and further includes means for closing said opening when no endoscope is positioned therein.

9. A method of attaching a respiratory system accessory device to a respiratory support system by means of an adaptor for use of the respiratory system accessory device on a patient, the respiratory support system including a manifold which is in fluid flow connection between the patient and a ventilator circuit, the manifold including a normally closed accessory access port and the adaptor including an opening means, said method steps including: removably inserting a portion of the adaptor including the opening means into the normally closed accessory access port of the manifold to Open the normally closed accessory access port to allow fluid flow access between the manifold and the adaptor,
    removably attaching a respiratory system accessory device to the adaptor,
    using the respiratory system accessory device on the patient, and
    removing the adaptor from the manifold.

10. The method of claim 9 wherein said step of attaching a respiratory system accessory device to the manifold includes attaching a metered dose injection canister to the adaptor.

11. The method of claim 9 wherein said step of attaching a respiratory system accessory device to the adaptor includes attaching an ambulatory resuscitation bag to the adaptor.

12. The method of claim 9 wherein said step of attaching a respiratory system accessory device to the adaptor includes attaching an endoscope to the adaptor.

* * * * *